(12) United States Patent
Gault et al.

(10) Patent No.: US 11,213,327 B2
(45) Date of Patent: Jan. 4, 2022

(54) FRACTURE PLATES, SYSTEMS, AND METHODS

(71) Applicant: GLOBUS MEDICAL, INC., Audubon, PA (US)

(72) Inventors: James A. Gault, Philadelphia, PA (US); Andrew Davison, Downingtown, PA (US); Alex Bada, Ardmore, PA (US); John Scolaro, Irvine, CA (US)

(73) Assignee: Globus Medical, Inc., Audubon, PA (US)

( * ) Notice: Subject to any disclaimer, the term of this patent is extended or adjusted under 35 U.S.C. 154(b) by 165 days.

(21) Appl. No.: 15/587,473

(22) Filed: May 5, 2017

(65) Prior Publication Data

US 2018/0049784 A1    Feb. 22, 2018

Related U.S. Application Data

(63) Continuation-in-part of application No. 15/420,143, filed on Jan. 31, 2017, now Pat. No. 10,575,884, which is a continuation-in-part of application No. 15/405,368, filed on Jan. 13, 2017, now Pat. No. 10,751,098, which is a continuation-in-part of application No. 15/238,772, filed on Aug. 17, 2016, now Pat. No. 10,687,873.

(51) Int. Cl.
*A61B 17/80* (2006.01)
*A61B 17/84* (2006.01)
*A61B 17/86* (2006.01)

(52) U.S. Cl.
CPC ........ *A61B 17/8014* (2013.01); *A61B 17/809* (2013.01); *A61B 17/8057* (2013.01); *A61B 17/8061* (2013.01); *A61B 17/848* (2013.01); *A61B 17/8605* (2013.01)

(58) Field of Classification Search
CPC ... A61B 17/80; A61B 17/8014; A61B 17/809; A61B 17/848; A61B 17/8061; A61B 17/8057; A61B 17/0401; A61B 2017/0404
USPC .............................. 606/70–71, 280–321, 232
See application file for complete search history.

(56) References Cited

U.S. PATENT DOCUMENTS

| | | |
|---|---|---|
| 1,105,105 A | 7/1914 | Sherman |
| 2,486,303 A | 10/1949 | Longfellow |
| 3,716,050 A | 2/1973 | Johnston |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |
| 4,781,183 A | 11/1988 | Casey et al. |
| 4,867,144 A | 9/1989 | Karas et al. |
| 5,002,544 A | 3/1991 | Klaue et al. |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — Jessica Weiss

(57) ABSTRACT

Devices, systems, and methods of bone stabilization. The bone stabilization system includes a bone plate having an upper surface and a lower surface configured to be in contact with bone, the bone plate having an opening extending from the upper surface to the lower surface. The opening is configured to receive a fastener, which may be either a locking fastener or a compression fastener.

20 Claims, 12 Drawing Sheets

(56) References Cited

U.S. PATENT DOCUMENTS

| | | | |
|---|---|---|---|
| 5,041,114 A | 8/1991 | Chapman et al. | |
| 5,151,103 A | 9/1992 | Tepic et al. | |
| 5,259,398 A | 11/1993 | Vrespa | |
| 5,364,399 A | 11/1994 | Lowery et al. | |
| 5,372,598 A | 12/1994 | Luhr et al. | |
| 5,423,826 A | 6/1995 | Coates et al. | |
| 5,601,553 A | 2/1997 | Trebing et al. | |
| 5,676,667 A | 10/1997 | Hausman | |
| 5,709,686 A | 1/1998 | Talos et al. | |
| 5,718,704 A | 2/1998 | Medoff | |
| 5,746,742 A | 5/1998 | Runciman et al. | |
| 5,785,712 A | 7/1998 | Runciman et al. | |
| 5,938,664 A | 8/1999 | Winquist et al. | |
| 6,001,099 A | 12/1999 | Huebner | |
| 6,096,040 A | 8/2000 | Esser | |
| 6,152,927 A | 11/2000 | Farris et al. | |
| 6,206,881 B1 | 3/2001 | Frigg et al. | |
| 6,283,969 B1 | 9/2001 | Grusin et al. | |
| 6,309,393 B1 | 10/2001 | Tepic et al. | |
| 6,322,562 B1 | 11/2001 | Wolter | |
| 6,364,882 B1 | 4/2002 | Orbay | |
| 6,533,786 B1 | 3/2003 | Needham et al. | |
| 6,623,486 B1 | 9/2003 | Weaver et al. | |
| 6,669,700 B1 | 12/2003 | Farris et al. | |
| 6,669,701 B2 | 12/2003 | Steiner et al. | |
| 6,712,820 B2 | 3/2004 | Orbay | |
| 6,719,759 B2 | 4/2004 | Wagner et al. | |
| 6,730,091 B1 | 5/2004 | Pfefferle et al. | |
| 6,866,665 B2 | 3/2005 | Orbay | |
| 6,955,677 B2 | 10/2005 | Dahners | |
| 6,974,461 B1 | 12/2005 | Wolter | |
| 7,001,387 B2 | 2/2006 | Farris et al. | |
| 7,063,701 B2 | 6/2006 | Michelson | |
| 7,128,744 B2 | 10/2006 | Weaver et al. | |
| 7,137,987 B2 | 11/2006 | Patterson et al. | |
| 7,153,309 B2 | 12/2006 | Huebner et al. | |
| 7,179,260 B2 | 2/2007 | Gerlach et al. | |
| 7,250,053 B2 | 7/2007 | Orbay | |
| 7,294,130 B2 | 11/2007 | Orbay | |
| 7,322,983 B2 | 1/2008 | Harris | |
| 7,341,589 B2 | 3/2008 | Weaver et al. | |
| 7,354,441 B2 | 4/2008 | Frigg | |
| 7,604,657 B2 | 10/2009 | Orbay et al. | |
| 7,632,277 B2 | 12/2009 | Woll et al. | |
| 7,635,381 B2 | 12/2009 | Orbay | |
| 7,637,928 B2 | 12/2009 | Fernandez | |
| 7,655,029 B2 | 2/2010 | Niedernberger et al. | |
| 7,695,472 B2 | 4/2010 | Young | |
| 7,722,653 B2 | 5/2010 | Young et al. | |
| 7,740,648 B2 | 6/2010 | Young et al. | |
| 7,776,076 B2 | 8/2010 | Grady, Jr. et al. | |
| 7,857,838 B2 | 12/2010 | Orbay | |
| 7,867,260 B2 | 1/2011 | Meyer et al. | |
| 7,867,261 B2 | 1/2011 | Sixto, Jr. et al. | |
| 7,875,062 B2 | 1/2011 | Lindemann et al. | |
| 7,905,910 B2 | 3/2011 | Gerlach et al. | |
| 7,909,858 B2 | 3/2011 | Gerlach et al. | |
| 7,951,176 B2 * | 5/2011 | Grady, Jr. | A61B 17/746 606/280 |
| 7,951,178 B2 | 5/2011 | Jensen | |
| 7,951,179 B2 | 5/2011 | Matityahu | |
| 7,976,570 B2 | 7/2011 | Wagner et al. | |
| D643,121 S | 8/2011 | Millford et al. | |
| D646,785 S | 10/2011 | Milford | |
| 8,043,297 B2 | 10/2011 | Grady, Jr. et al. | |
| 8,057,520 B2 | 11/2011 | Ducharme et al. | |
| 8,062,296 B2 | 11/2011 | Orbay et al. | |
| 8,100,953 B2 | 1/2012 | White et al. | |
| 8,105,367 B2 | 1/2012 | Austin et al. | |
| 8,114,081 B2 | 2/2012 | Kohut et al. | |
| 8,118,846 B2 | 2/2012 | Leither et al. | |
| 8,162,950 B2 | 4/2012 | Digeser et al. | |
| 8,167,918 B2 | 5/2012 | Stmad et al. | |
| 8,177,820 B2 | 5/2012 | Anapliotis et al. | |
| 8,246,661 B2 | 8/2012 | Beutter et al. | |
| 8,252,032 B2 | 8/2012 | White et al. | |
| 8,257,403 B2 | 9/2012 | Den Hartog et al. | |
| 8,257,405 B2 | 9/2012 | Haidukewych et al. | |
| 8,257,406 B2 | 9/2012 | Kay et al. | |
| 8,262,707 B2 | 9/2012 | Huebner et al. | |
| 8,267,972 B1 * | 9/2012 | Gehlert | A61B 17/746 606/280 |
| 8,317,842 B2 | 11/2012 | Graham et al. | |
| 8,323,321 B2 | 12/2012 | Gradl | |
| 8,337,535 B2 | 12/2012 | White et al. | |
| 8,343,155 B2 | 1/2013 | Fisher et al. | |
| 8,382,807 B2 | 2/2013 | Austin et al. | |
| 8,394,098 B2 | 3/2013 | Orbay et al. | |
| 8,394,130 B2 | 3/2013 | Orbay et al. | |
| 8,398,685 B2 | 3/2013 | McGarity et al. | |
| 8,403,966 B2 | 3/2013 | Ralph et al. | |
| 8,419,775 B2 | 4/2013 | Orbay et al. | |
| 8,435,272 B2 | 5/2013 | Dougherty et al. | |
| 8,439,918 B2 | 5/2013 | Gelfand | |
| 8,444,679 B2 | 5/2013 | Ralph et al. | |
| 8,491,593 B2 | 7/2013 | Prien et al. | |
| 8,506,608 B2 | 8/2013 | Cerynik et al. | |
| 8,512,385 B2 | 8/2013 | White et al. | |
| 8,518,090 B2 | 8/2013 | Huebner et al. | |
| 8,523,862 B2 | 9/2013 | Murashko, Jr. | |
| 8,523,919 B2 | 9/2013 | Huebner et al. | |
| 8,523,921 B2 | 9/2013 | Horan et al. | |
| 8,551,095 B2 | 10/2013 | Fritzinger et al. | |
| 8,568,462 B2 | 10/2013 | Sixto, Jr. et al. | |
| 8,574,268 B2 | 11/2013 | Chan et al. | |
| 8,597,334 B2 | 12/2013 | Mocanu | |
| 8,603,147 B2 | 12/2013 | Sixto, Jr. et al. | |
| 8,617,224 B2 | 12/2013 | Kozak et al. | |
| 8,632,574 B2 | 1/2014 | Kortenbach et al. | |
| 8,641,741 B2 | 2/2014 | Murashko, Jr. | |
| 8,641,744 B2 | 2/2014 | Weaver et al. | |
| 8,663,224 B2 | 3/2014 | Overes et al. | |
| 8,728,082 B2 | 5/2014 | Fritzinger et al. | |
| 8,728,126 B2 | 5/2014 | Steffen | |
| 8,740,905 B2 | 6/2014 | Price et al. | |
| 8,747,442 B2 | 6/2014 | Orbay et al. | |
| 8,764,751 B2 | 7/2014 | Orbay et al. | |
| 8,764,808 B2 | 7/2014 | Gonzalez-Hernandez | |
| 8,777,998 B2 | 7/2014 | Daniels et al. | |
| 8,790,376 B2 | 7/2014 | Fritzinger et al. | |
| 8,790,377 B2 | 7/2014 | Ralph et al. | |
| 8,808,333 B2 | 8/2014 | Kuster et al. | |
| 8,808,334 B2 | 8/2014 | Strnad et al. | |
| 8,834,532 B2 | 9/2014 | Velikov et al. | |
| 8,834,537 B2 | 9/2014 | Castanada et al. | |
| 8,852,246 B2 | 10/2014 | Hansson | |
| 8,852,249 B2 | 10/2014 | Ahrens et al. | |
| 8,864,802 B2 | 10/2014 | Schwager et al. | |
| 8,870,931 B2 | 10/2014 | Dahners et al. | |
| 8,888,825 B2 | 11/2014 | Batsch et al. | |
| 8,906,076 B2 | 12/2014 | Mocanu et al. | |
| 8,911,482 B2 | 12/2014 | Lee et al. | |
| 8,926,675 B2 | 1/2015 | Leung et al. | |
| 8,940,026 B2 | 1/2015 | Hilse et al. | |
| 8,940,028 B2 | 1/2015 | Austin et al. | |
| 8,940,029 B2 | 1/2015 | Leung et al. | |
| 8,951,291 B2 | 2/2015 | Impellizzeri | |
| 8,968,368 B2 | 3/2015 | Tepic | |
| 9,011,457 B2 | 4/2015 | Grady, Jr. et al. | |
| 9,023,052 B2 | 5/2015 | Lietz et al. | |
| 9,050,151 B2 | 6/2015 | Schilter | |
| 9,072,555 B2 | 7/2015 | Michel | |
| 9,072,557 B2 | 7/2015 | Fierlbeck et al. | |
| 9,107,678 B2 | 8/2015 | Murner et al. | |
| 9,107,711 B2 | 8/2015 | Hainard | |
| 9,107,713 B2 | 8/2015 | Horan et al. | |
| 9,107,718 B2 | 8/2015 | Isch | |
| 9,113,970 B2 | 8/2015 | Lewis et al. | |
| 9,149,310 B2 | 10/2015 | Fritzinger et al. | |
| 9,161,791 B2 | 10/2015 | Frigg | |
| 9,161,795 B2 | 10/2015 | Chasbrummel et al. | |
| 9,168,075 B2 | 10/2015 | Dell'Oca | |
| 9,179,950 B2 | 11/2015 | Zajac et al. | |
| 9,179,956 B2 | 11/2015 | Cerynik et al. | |

(56) References Cited

U.S. PATENT DOCUMENTS

| | | | |
|---|---|---|---|
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,566,097 B2 | 2/2017 | Fierlbeck et al. |
| 9,636,157 B2 | 5/2017 | Medoff |
| 9,649,141 B2 | 5/2017 | Raven, III et al. |
| 9,668,794 B2 | 6/2017 | Kuster et al. |
| 2002/0045901 A1 | 4/2002 | Wagner et al. |
| 2004/0097937 A1 | 5/2004 | Pike et al. |
| 2004/0167522 A1* | 8/2004 | Niederberger | A61B 17/8061 606/286 |
| 2005/0010226 A1* | 1/2005 | Grady, Jr. | A61B 17/746 606/281 |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0009771 A1* | 1/2006 | Orbay | A61B 17/8057 606/291 |
| 2006/0122602 A1* | 6/2006 | Konieczynski | A61B 17/7059 606/281 |
| 2006/0149265 A1 | 7/2006 | James et al. |
| 2006/0173458 A1* | 8/2006 | Forstein | A61B 17/1728 606/86 B |
| 2006/0241607 A1 | 10/2006 | Myerson et al. |
| 2007/0270849 A1* | 11/2007 | Orbay | A61B 17/74 606/291 |
| 2008/0021477 A1 | 1/2008 | Strnad et al. |
| 2008/0051786 A1* | 2/2008 | Jensen | A61B 17/8057 606/86 A |
| 2008/0161860 A1 | 7/2008 | Ahrens et al. |
| 2008/0234749 A1 | 9/2008 | Forstein |
| 2008/0275510 A1 | 11/2008 | Schonhardt et al. |
| 2008/0300637 A1* | 12/2008 | Austin | A61B 17/74 606/290 |
| 2009/0024172 A1* | 1/2009 | Pizzicara | A61B 17/8014 606/280 |
| 2009/0024173 A1 | 1/2009 | Reis, Jr. |
| 2009/0118773 A1 | 5/2009 | James et al. |
| 2009/0143825 A1 | 6/2009 | Graham et al. |
| 2009/0198285 A1 | 8/2009 | Raven, III |
| 2009/0228010 A1* | 9/2009 | Gonzalez-Hernandez | A61B 17/80 606/70 |
| 2009/0228047 A1 | 9/2009 | Derouet et al. |
| 2009/0248084 A1 | 10/2009 | Hintermann |
| 2009/0281543 A1 | 11/2009 | Orbay et al. |
| 2009/0312759 A1* | 12/2009 | Ducharme | A61B 17/8061 606/70 |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0249850 A1* | 9/2010 | Cerynik | A61B 17/72 606/281 |
| 2010/0274247 A1 | 10/2010 | Grady, Jr. et al. |
| 2011/0071573 A1* | 3/2011 | Sixto | A61B 17/8014 606/286 |
| 2011/0106086 A1 | 5/2011 | Laird |
| 2011/0218580 A1 | 9/2011 | Schwager et al. |
| 2012/0059424 A1 | 3/2012 | Epperly et al. |
| 2012/0265254 A1* | 10/2012 | Horan | A61B 17/8061 606/289 |
| 2012/0323284 A1 | 12/2012 | Baker et al. |
| 2013/0018426 A1 | 1/2013 | Tsai et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0184765 A1* | 7/2013 | Beyar | A61B 17/8052 606/281 |
| 2013/0211463 A1 | 8/2013 | Mizuno et al. |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer |
| 2014/0330320 A1 | 11/2014 | Wolter |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0094775 A1 | 4/2015 | Batsch et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0157373 A1 | 6/2015 | Wolf et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2016/0022336 A1 | 1/2016 | Bateman |
| 2016/0030035 A1* | 2/2016 | Zajac | A61B 17/0401 606/281 |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1* | 6/2016 | Mighell | A61B 17/8057 606/291 |
| 2016/0166298 A1 | 6/2016 | Mighell et al. |
| 2016/0262814 A1 | 9/2016 | Wainscott |
| 2016/0278828 A1 | 9/2016 | Ragghianti |
| 2016/0310183 A1 | 10/2016 | Shaw et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0056081 A1 | 3/2017 | Langdale et al. |
| 2017/0065312 A1 | 3/2017 | Lauf et al. |
| 2017/0215931 A1 | 8/2017 | Cremer et al. |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| EP | 2227160 A2 | 9/2010 |

(56) References Cited

FOREIGN PATENT DOCUMENTS

| | | |
|---|---|---|
| EP | 2273943 A1 | 1/2011 |
| FR | 2846870 A1 | 5/2004 |
| FR | 2928259 A1 | 9/2009 |
| JP | 2003210478 A | 7/2003 |
| TW | 201316942 A | 5/2013 |
| WO | 2016079504 A1 | 5/2016 |

* cited by examiner

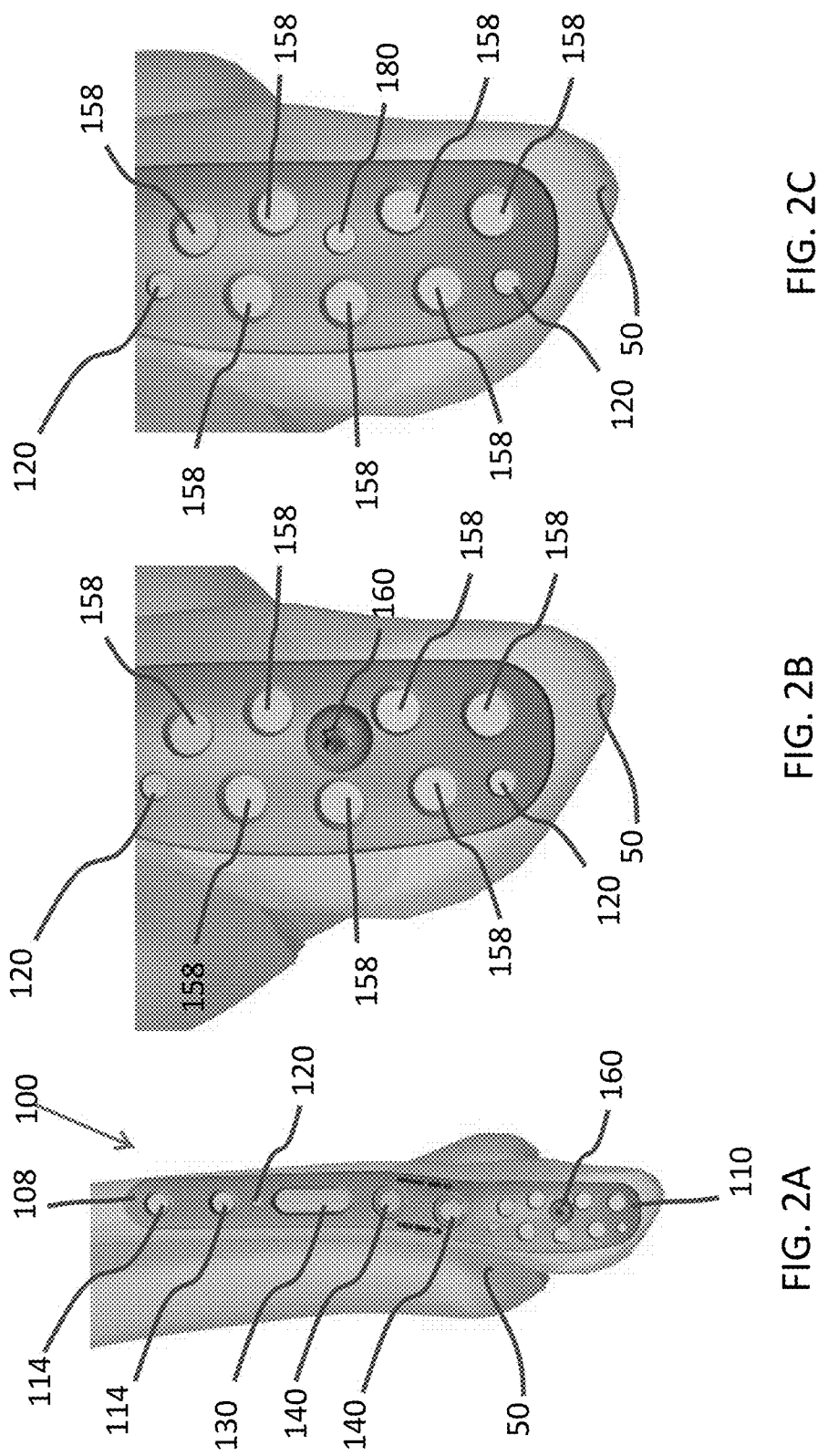

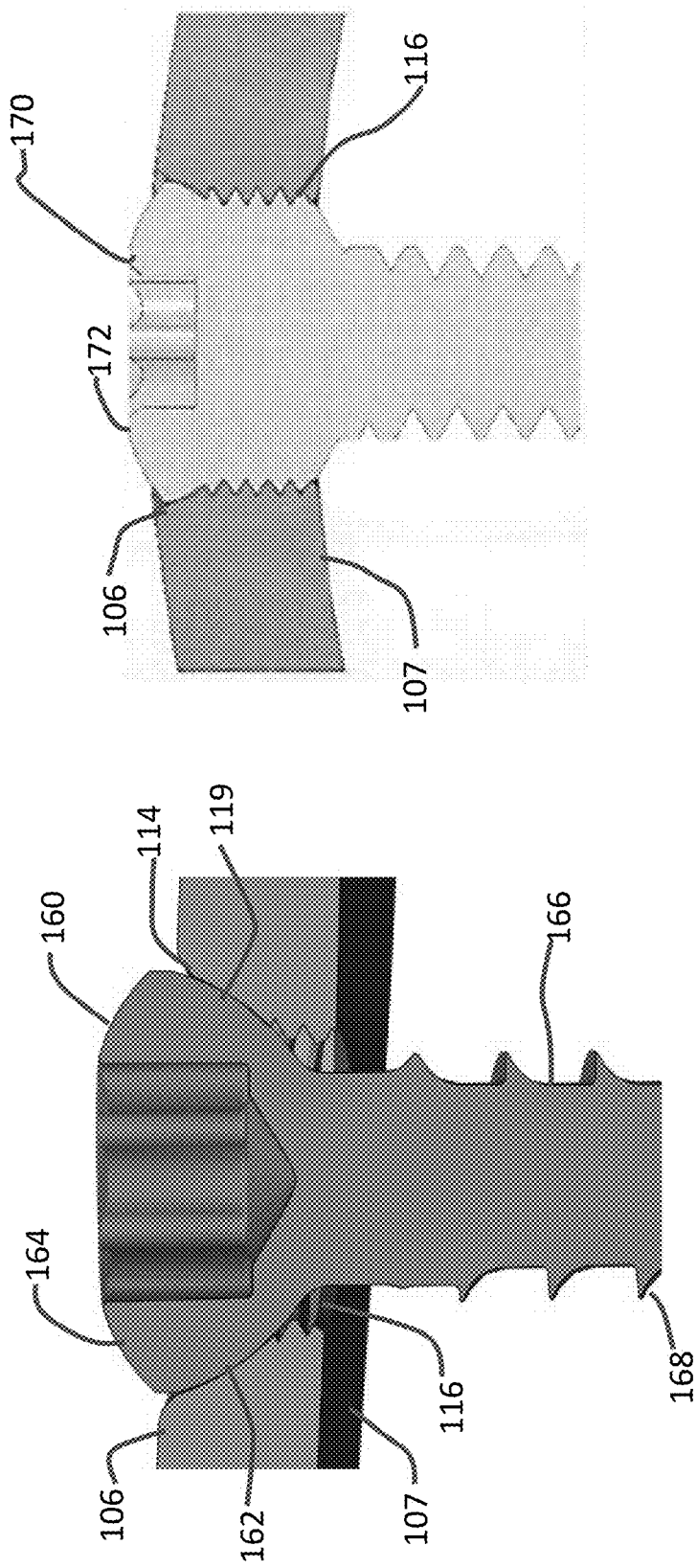

FRACTURE PLATES, SYSTEMS, AND METHODS

CROSS-REFERENCE TO RELATED APPLICATIONS

The present application is a continuation-in-part of U.S. patent application Ser. No. 15/420,143, filed Jan. 31, 2017, which is a continuation-in-part of U.S. patent application Ser. No. 15/405,368, filed Jan. 13, 2017, which is a continuation-in-part of U.S. patent application Ser. No. 15/238,772, filed Aug. 17, 2016, which are hereby incorporated by reference in their entireties for all purposes.

FIELD

The present disclosure relates to surgical devices, and more particularly, stabilization systems, for example, for trauma applications.

BACKGROUND

Bone fractures are often repaired by internal fixation of the bone, such as diaphyseal bone, including tibia and fibula bones, using one or more plates. The plate is held against the fractured bone with screws, for example, which engage the bone and heads which provide a compressive force against the plate. The plate and bone are thus forced against each other in a manner that transfers load primarily between a bone contacting surface of the plate and the bone surface to reinforce the fractured bone during healing. This manner of plating generally creates relatively low stress concentration in the bone, as there may be a large contact area between the plate and the diaphyseal bone surface permitting transfer of load to be dispersed. There may be a desire to use locking screws, non-locking screws, or a combination of both that are able to dynamically compress the bone. Of course, the designs of the plates, types of screws, and locking and/or non-locking capabilities may vary based on the location and type of fracture.

Accordingly, there is a need for plating systems that provide stabilization to the appropriate anatomical area while providing appropriate locking and/or unlocking capability for dynamic compression of the bone.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to embodiments, a stabilization system may include a plurality of plates configured to fix bone in the treatment of ankle fractures. Anatomic bone plates facilitate the well-known and established treatment methods for bone fractures. An advantage of the exemplary stabilization systems is the availability to use various treatment options. It is often a surgeon's preference whether to use a screw or a suture button system to repair a syndesmosis, and it is advantageous to provide a plate that can accept either.

In one embodiment, the stabilization system comprises a bone plate having an upper surface and a lower surface configured to be in contact with bone. The bone plate has a through-opening extending from the upper surface to the lower surface. The through-opening includes a threaded portion proximate to the lower surface and a non-threaded portion proximate to the upper surface. A fastener is configured to engage the through-opening and to secure the bone plate to the bone. The through-opening is configured to receive one of a locking fastener and a compression fastener.

In an alternative embodiment, the stabilization system comprises a bone plate having an upper surface and a lower surface configured to be in contact with bone. The bone plate has a through-opening extending from the upper surface to the lower surface. The through-opening includes a threaded portion proximate to the lower surface and a non-threaded portion proximate to the upper surface. A locking fastener is configured to be received by the through-opening and configured to be inserted into the bone. The locking fastener has a threaded head portion configured to lock to the bone plate. A compression fastener is configured to be received by the through-opening and configured to be inserted into the bone. The compression fastener has a substantially smooth portion configured to dynamically compress the bone.

In still another alternative embodiment, a stabilization system comprises a bone plate having an upper surface and a lower surface configured to be in contact with bone. The bone plate has a through-opening extending from the upper surface to the lower surface. The through-opening is formed by at least three different co-axial bores including a first bore having an internal thread and a first diameter; a second bore having an unthreaded conical side wall and a second diameter, greater than the first diameter; and a third bore having an annular surface surrounding the side wall and a third diameter, greater than the second diameter.

In another embodiment, a stabilization system comprises a bone plate having an elongate body extending from a proximal end to a distal end along a longitudinal axis and having an enlarged head portion proximate the distal end, wherein the bone plate is generally symmetric about the longitudinal axis, the bone plate having an elongated slot located along the longitudinal axis having a length greater than its width, the bone plate having a plurality of syndesmotic openings located along the longitudinal axis, wherein one of the syndesmotic openings is located adjacent to the elongated slot, the syndesmotic openings being sized and dimensioned to accept a suture button, a non-locking screw, or a locking screw, and the bone plate having a plurality of openings in the enlarged head portion.

In yet another embodiment, a stabilization system comprises a bone plate having an elongate body extending from a proximal end to a distal end along a longitudinal axis and having an enlarged head portion proximate the distal end, wherein the bone plate is symmetric about the longitudinal axis, the bone plate having first and second stacked openings located along the longitudinal axis and positioned proximate to the proximal end of the bone plate, the first and second stacked openings configured to accept either locking or non-locking fasteners, the bone plate having an elongated slot located along the longitudinal axis having a length greater than its width, wherein the elongated slot is located adjacent to the second stacked opening, the bone plate having a plurality of syndesmotic openings located along the longitudinal axis, wherein one of the syndesmotic openings is located adjacent to the elongated slot, the syndesmotic openings being sized and dimensioned to accept a suture button, a non-locking screw, or a locking screw, and the bone plate having a plurality of openings in the enlarged head portion.

Also provided are additional stabilization systems, bone plates, methods for installing the stabilization systems, and kits including bone plates, fasteners, and components for installing the same.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 2A-2C is an alternative lateral distal fibula plate according to another embodiment;

FIG. 3A is a sectional view of a first (shaft) through-opening extending through the lateral distal fibula plate shown in FIG. 1A with a non-locking fastener inserted in the through-opening;

FIG. 3B is a sectional view of the first through-opening extending through the lateral distal fibula plate shown in FIG. 1A with a locking fastener inserted in the through-opening;

DETAILED DESCRIPTION

Figure 1A:
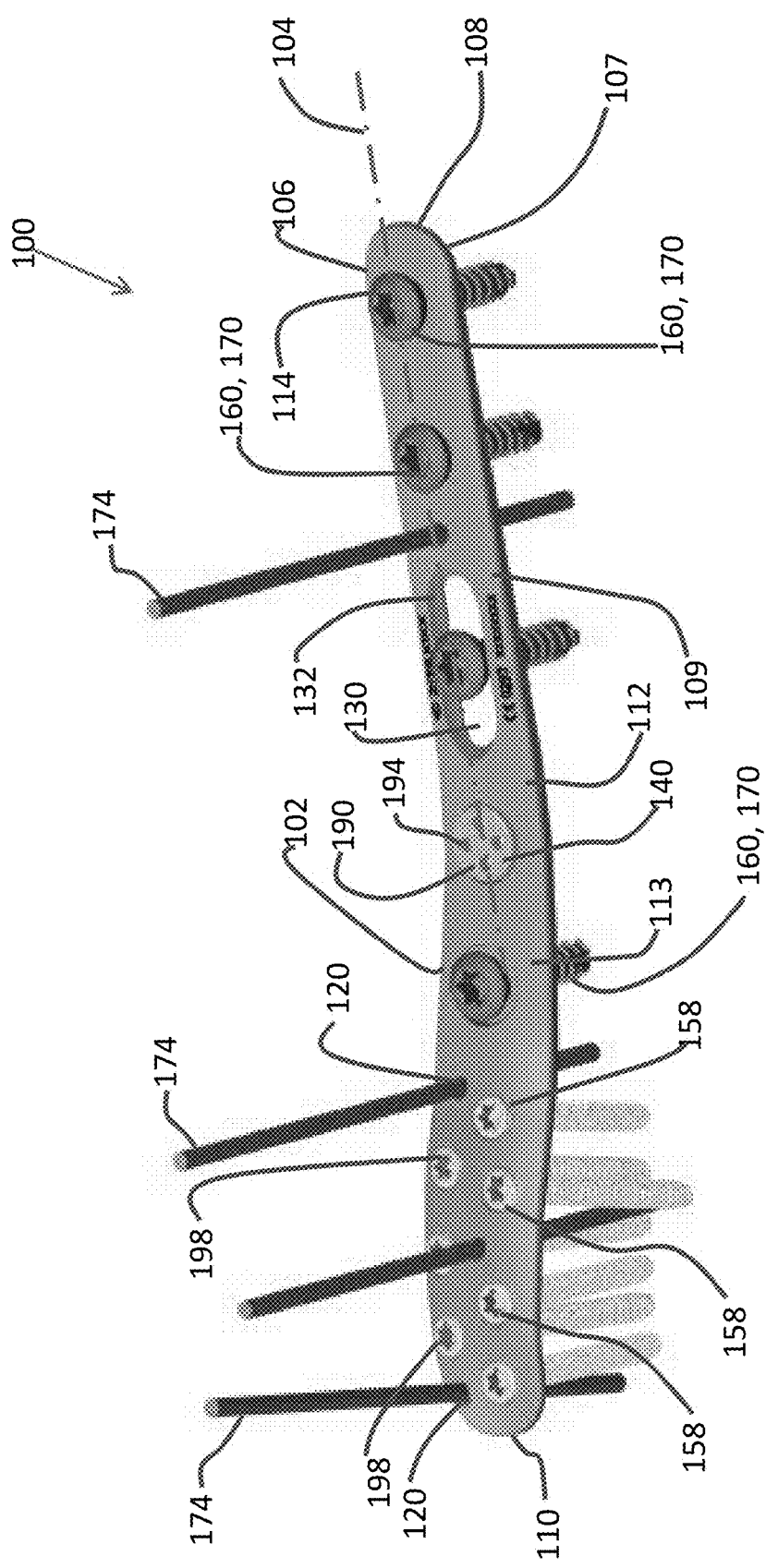
FIG. 1A is a perspective view of a lateral distal fibula plate according to a first exemplary embodiment.
Figure 1B:
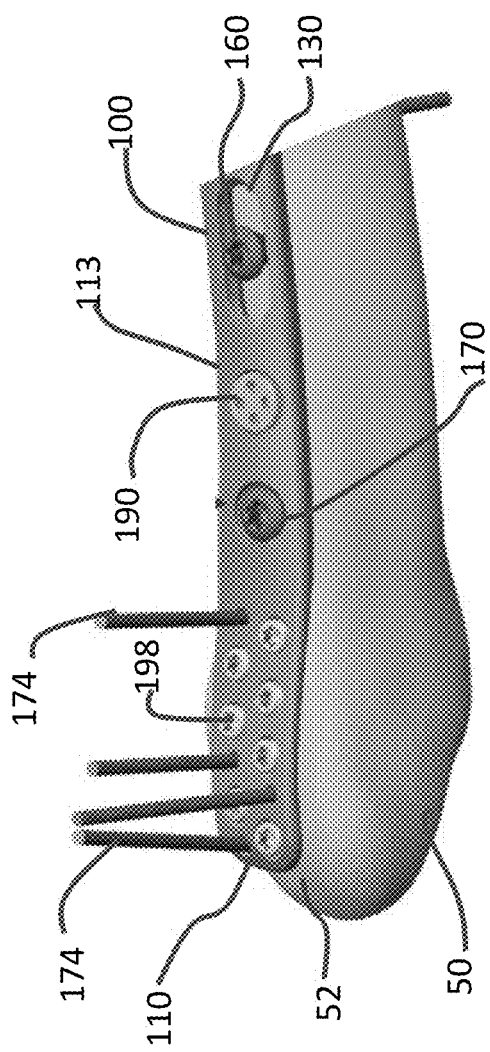
FIG. 1B is an enlarged view of a distal end of the lateral distal fibula plate shown in FIG. 1A affixed to a bone.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required. Conversely, the terms "directly coupled," "directly connected," etc., imply the absence of such additional elements.

The present disclosure provides embodiments of plates, securing devices, systems, and associated methods that can be used to repair, for example, bone fractures, particularly ankle fractures.

Specifically, embodiments are directed to bone plating with locking and/or non-locking fasteners for dynamic compression of bone. The hole designs may allow for fixed angle and/or polyaxial locking and/or non-locking of the fasteners. Some embodiments include locking fasteners with self-forming threads configured to displace the plate material, thereby locking the fastener to the plate.

While exemplary embodiments of the plates are used to repair ankle fractures, those skilled in the art will recognize that the plates may be adapted to contact one or more of a femur, a distal tibia, a proximal tibia, a proximal humerus, a distal humerus, a clavicle, a fibula, an ulna, a radius, bones of the foot, bones of the hand, or other suitable bone or bones. The bone plate may be curved, contoured, straight, or flat. The plate may have a head portion that is contoured to match a particular bone surface, such as a metaphysis or diaphysis, flares out from the shaft portion, forms an L-shape, T-shape, Y-shape, etc., with the shaft portion, or that forms any other appropriate shape to fit the anatomy of the bone to be treated.

The bone plate may be comprised of titanium, stainless steel, cobalt chrome, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the fasteners may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and fasteners are made, it should be understood that bone plates and fasteners comprised of any appropriate material are contemplated.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law.

Figure 4:
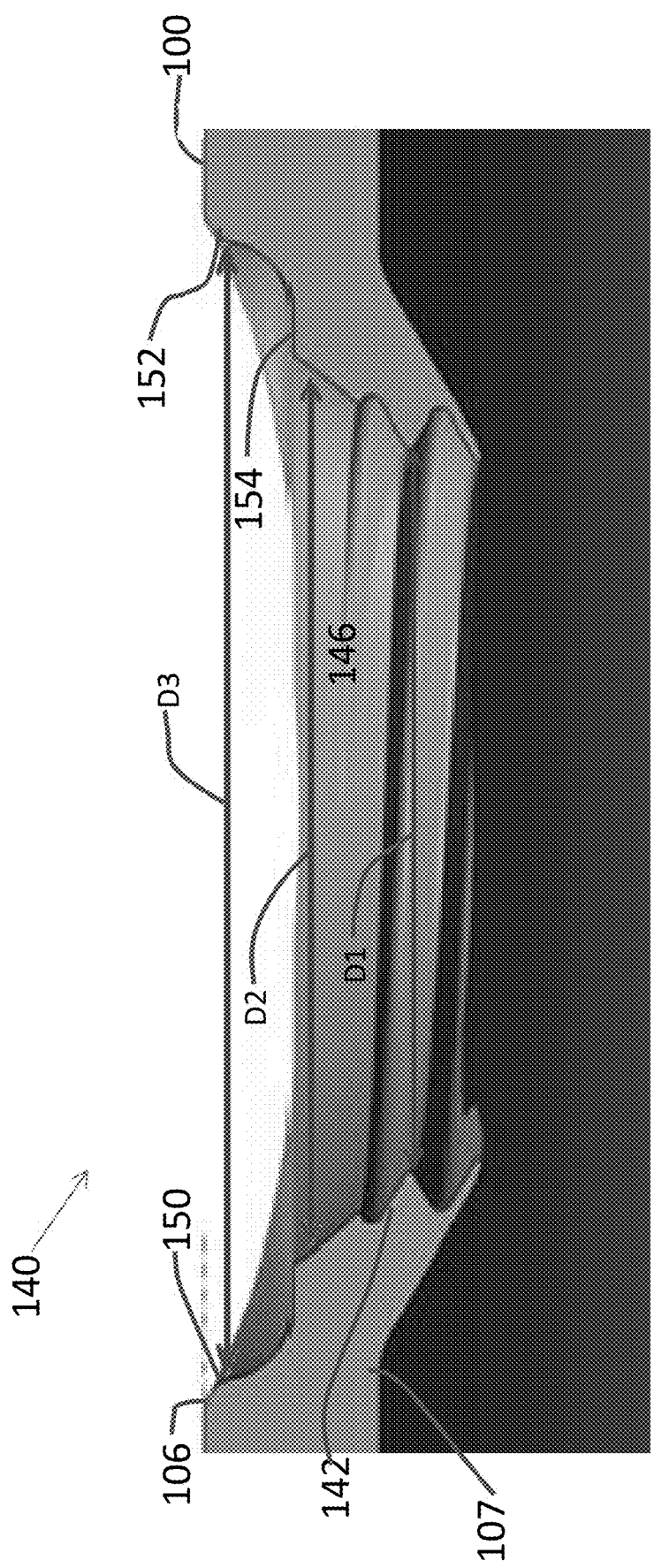
FIG. 4 is a sectional view of a second (syndesmotic) hole extending through the lateral distal fibula plate shown in FIG. 1A.
Figure 5:
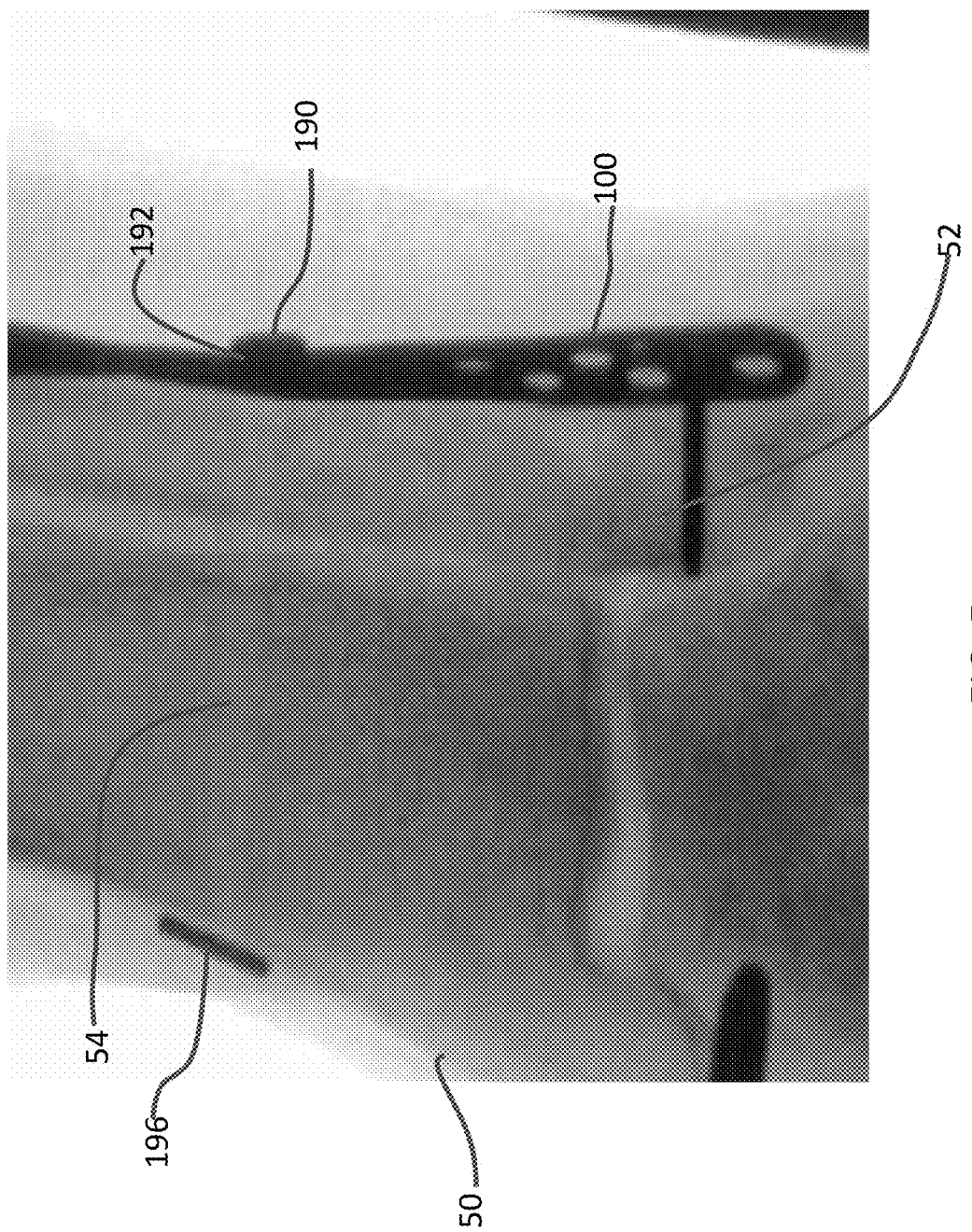
FIG. 5 is an x-ray showing the lateral distal fibula plate shown in FIG. 1 fixed to a broken fibula.

Referring to FIGS. 1-5, a lateral distal fibula plate 100 ("plate 100") according to a first exemplary embodiment is shown. Referring specifically to FIGS. 1B and 5, plate 100 is fixed to the lateral surface 52 of a fibula 50. Plate 100 may be used to treat fractures of the distal fibula 50 and/or disruption of the syndesmosis, and can have a pre-contoured shape, such as is shown in FIG. 1A. Alternatively, plate 100 can be contoured prior to use in order to conform to a particular bone structure.

Plate 100 has an elongate body 102 extending generally along a central longitudinal axis 104. Plate 100 has an upper surface 106 extending between a proximal end 108 and a distal end 110 and a lower surface 107 configured to be in contact with bone. A body portion 112 extends between proximal end 108 and distal end 110 and has a transition section 113 where body portion 112 transitions from a generally planar portion 109 proximate to proximal end 108 and a contoured portion 111 proximate to distal end 110.

As used herein, the term "contoured" means "curved" such that contoured portion 111 includes surfaces (upper surface 106, lower surface 107, or both) with non-infinite radii. The contours do not necessarily need to be constant; the radius of curvature of contoured portion 111 can vary along the length and width of contoured portion 111. In an exemplary embodiment, contoured portion 111 can be contoured to match the contours of the bone to which plate 100 is to be fixed, such as a fibula.

In an exemplary embodiment, proximal end 108 and distal end 110 each includes a smooth, rounded ends and edges. Body portion 112 is contoured, with smooth, rounded edges. The smooth, rounded ends and edges eliminate the potential for inadvertently engaging and ripping any adjoining tissue.

Body portion 112 also includes a plurality of different types of through-openings formed therein and extending from upper surface 106 to lower surface 107. The different types of through-openings disclosed in plate 100 will discussed from proximal end 108 to distal end 110, although those skilled in the art will recognize that the through-openings can be located at different places, in different orders, and intermixed together throughout the length of plate 100.

Referring to FIG. 3A, through-openings 114 are shaft holes including a threaded portion 116 proximate to lower surface 107 and a non-threaded portion 118 proximate to upper surface 106. Through-openings 114 may extend along longitudinal axis 104.

Threaded portion 116 and non-threaded portion 118 are co-axial. The shaft holes can accept both locking and non-locking screws, resulting in a "stacked" design, in which a non-locking hole geometry, non-threaded portion 118, is on top of locking threaded portion 116 below.

Through-openings 114 can alternatively receive fasteners comprised of locking screws or non-locking (compression) screws. In exemplary embodiments, screw 160 can be 3.5 mm or 4.0 mm screws, for example.

FIG. 3A shows a non-locking screw 160 inserted into through-opening 114. Non-threaded portion 118 is generally conical in shape such that non-threaded portion 118 is wider near upper surface 106 of plate 100 and narrower toward threaded portion 116. Screw 160 has a substantially smooth convex portion 162 of a head 164 configured to be received by and engage with non-threaded portion 118 and to dynamically compress bone 50 after fixation of plate 100 to bone 50. Non-threaded portion 118 has a generally concave surface 119 to mate with convex surface portion 162 of head 164 of screw 160.

A shaft 166 of screw 160 has distal threads 168 that are configured to screw into bone 50. Shaft 166 and threads 168 have a narrower diameter than that of through-opening 114 so that shaft 166 can pass through through-opening 114 without engaging threaded portion 116 of through-opening 114.

A locking screw 170 is shown in FIG. 3B. Locking screw 170 has a threaded head portion 172 configured to engage threaded portion 116 of through-opening 114 and to lock screw 170 to plate 100. In some embodiments, threaded head portion 172 is a self-forming thread that is configured to displace material in threaded portion 116 of plate 100 to lock fastener 170 to plate 100.

A second type of through-opening 120, shown in FIG. 1A, may be sized and dimensioned to allow a K-wire 174 to pass therethrough. In an exemplary embodiment, through-opening 120 is sized to allow a 1.6 mm K-wire, to pass therethrough, although those skilled in the art will recognize that other size through-openings 120 can be provided for other size K-wires. As noted in FIG. 1A, one or more through-openings 120 are spaced along a length of plate 100 and are not necessarily aligned with longitudinal axis 104.

A third type of through-opening that can be provided in plate 100 is an elongate slot 130. Elongate slot 130 may extend along longitudinal axis 104, for example. The elongated slot 130 may have a length greater than its width, for example, a length two times its width, a length three times its width, or more. Elongate slot 130 may allow for a range of securing member insertion locations. In an exemplary embodiment, one elongate through-opening 130 is provided, although those skilled in the art will recognize, depending on the length of plate 100 and through-opening 130, one or more than through-opening 130 can be provided.

Slots 130 include generally smooth side walls to allow a securing member, such as screw 160, to be inserted at infinite locations along the length of each slot 130. A rib 132 extends around the inner perimeter of slot 130 below upper surface 106. In an exemplary embodiment, screws 130 can be 3.5 mm or 4.0 mm non-locking screws and can provide up to 1 mm of compression or distraction. Screws 160 may engage rib 132 along under surface 162 of head 164 of screw 160 so that head 164 is largely, if not entirely, within slot 130 to minimize the amount of head 162 extending above upper surface 106 of plate 100.

Referring to FIGS. 1A and 4, a fourth type of through-opening that can be provided in plate 100 is a syndesmotic hole 140 located at transition portion 113. Syndesmotic hole 140 can accept three different types of fixation: (1) a suture button 190; (2) non-locking screw 160; or (3) locking screw 170.

Referring specifically to the cross-section of hole 140 in FIG. 4, hole 140 includes, from lower surface 107 of plate 100 to upper surface 106 of plate 100, at least three different co-axial bores. A first bore includes a threaded portion 142, similar to threaded portion 116 of through-opening 114, with its bore having a first diameter D1.

Similar to through-opening 114, a second bore of hole 140 is has an unthreaded conical portion 144 with a conical side wall 146 located above and adjacent to threaded portion 142. The second bore of hole 140 has a maximum diameter D2, larger than diameter D1.

In contrast to through-opening 114, hole 140 further includes a third bore comprising a bowl portion 150 having a diameter D3, larger than maximum diameter D2. Bowl portion 150 is for the use of a suture button system that includes, for example, two metal buttons 190, 196, connected via suture. Button 196 interfaces with the far cortex of bone 50 (shown in FIG. 5), while button 190 interfaces with bone plate 100. This button system provides stability for a disrupted joint or bone fracture and also provides a type of mobile stability. The use of buttons 190, 196 may be a method of treatment for the syndesmosis when the syndesmosis is disrupted. Another type of fixation of a disrupted syndesmosis is a bone screw as described above, which is a more rigid fixation than the suture button system.

Referring to FIG. 4, bowl portion 150 is above and adjacent to conical portion 146. Conical portion 146 has a maximum diameter of diameter D2 proximate to bowl portion 150. Bowl portion 150 comprises a bowl diameter, larger than the maximum diameter. The transition between bowl portion 150 and threaded portion 142 (i.e. conical portion 144) is shown in FIG. 4 as a chamfer, but could alternatively be a round.

Bowl portion 150 includes a side wall 152 that circumscribes bowl portion 150 and an annular surface 154 between the side wall 152 and conical portion 144. Annular surface 154 surrounds side wall 146 of conical portion 144. Bowl portion 150 is configured to receive and retain a button 190 having a lower surface 192 (shown in FIG. 5) configured to engage annular surface 154 and fit within side wall 152.

Referring to FIG. 1A, button 190 also includes at least one thread hole 194 that is in communication with hole 140 when lower surface 192 is in engagement with annular surface 154.

Referring to FIG. 5, first button 190 is configured for insertion into bowl portion 150 of hole 140 and a second button 196 is configured to engage bone 50, distal from bone plate 100. A suture (not shown) extends through thread hole 194, through plate 100 and a passage 54 drilled through bone 50, to second button 196 to compress bone 50 and plate 100 between buttons 190, 196.

A fifth set of through holes 158 are provided at distal end 110 of plate 100. Holes 158 may be configured to receive locking screws 198. In an exemplary embodiment, holes 158 may be threaded to accept 2.5 mm locking screws 198, for example. A plurality of holes 158 (about seven as shown in plate 100) are provided to fix distal end 110 of plate 100 securely in bone 50. Holes 158 are not constrained along longitudinal axis 104 but instead are located along the width of plate 100 to provide a plurality of screw connections for a secure fixation to bone.

FIG. 2A depicts an alternative version of a lateral distal fibula plate 100. FIGS. 2B and 2C show close up views of the distal portion of the plate 100. The plate 100 is substantially the same as that disclosed in FIG. 1A, with the addition of a sixth type of through hole 180. This through hole 180 may be a non-threaded hole located within the distal head of the plate 100. Through hole 180 may have smaller diameter than the other distal through holes 158. The through hole 180 may be positioned near or surrounded by distal locking holes 158. The through hole 180 may be configured accept a non-locking fastener or screw 160 that can act as a suck-down screw. In a preferred embodiment, this hole 180 is not threaded. When used, the non-locking screw 160 may be placed first in order to get the plate 100 to be compressed down to the bone 50. This screw 160 can be left in after the other distal locking screws 198 are placed in holes 158 or screw 160 can be removed. As shown in FIGS. 2A-2C, the middle non-threaded hole 180 is configured to accept the non-locking screw 160, but it is envisioned that either a proximal or distal non-threaded hole 180 could accept a non-locking screw 160.

Figure 6A:
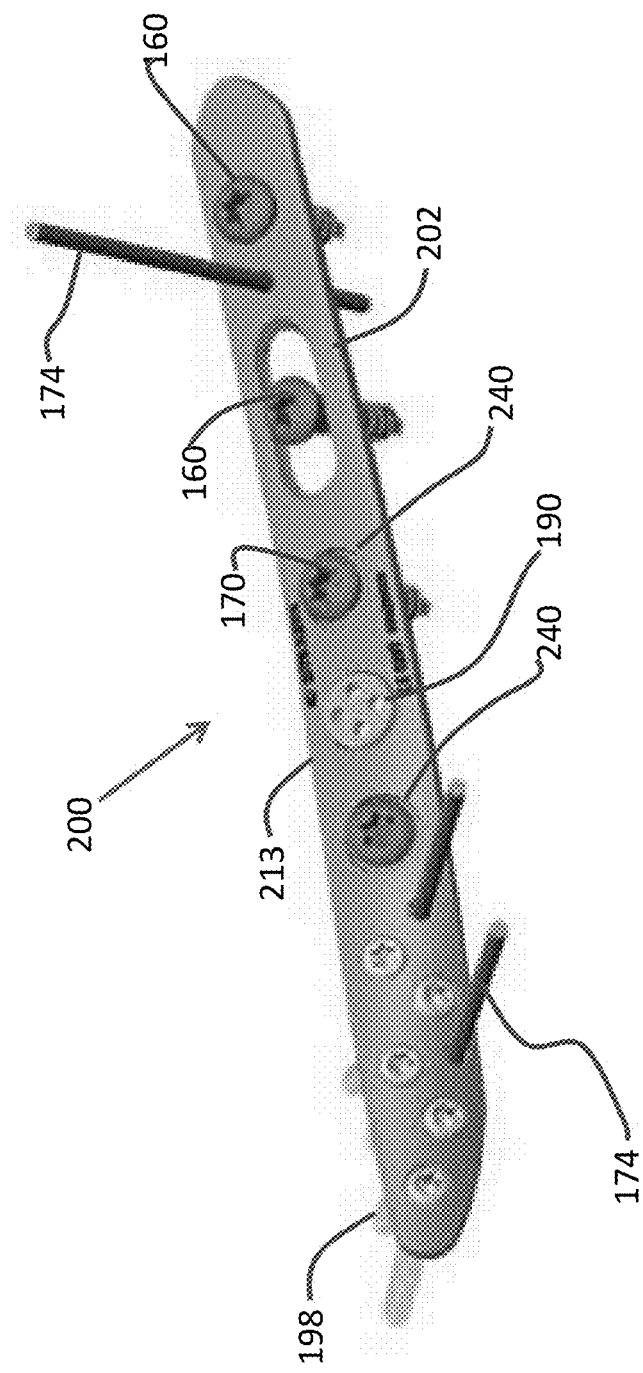
FIG. 6A is a perspective view of a posterolateral distal fibula plate according to a second exemplary embodiment.

A second embodiment of a plate 200, shown in FIG. 6A, is a posterolateral distal fibula plate. Plate 200 sits on the posterior face of the fibula distally, and wraps around to the lateral surface as plate 200 travels proximally. Plate 200 can be used to facilitate a posterior surgical approach. Similar to plate 100, plate 200 can have a variety of different through-openings, including syndesmotic holes 240, similar to syndesmotic holes 140 described above.

Plate 200 has a generally planar body 202 with a transition portion 213 proximate to syndesmotic holes 240, where body 202 transitions to a contoured shape to conform to the posterior face of the fibula.

Figure 6B:
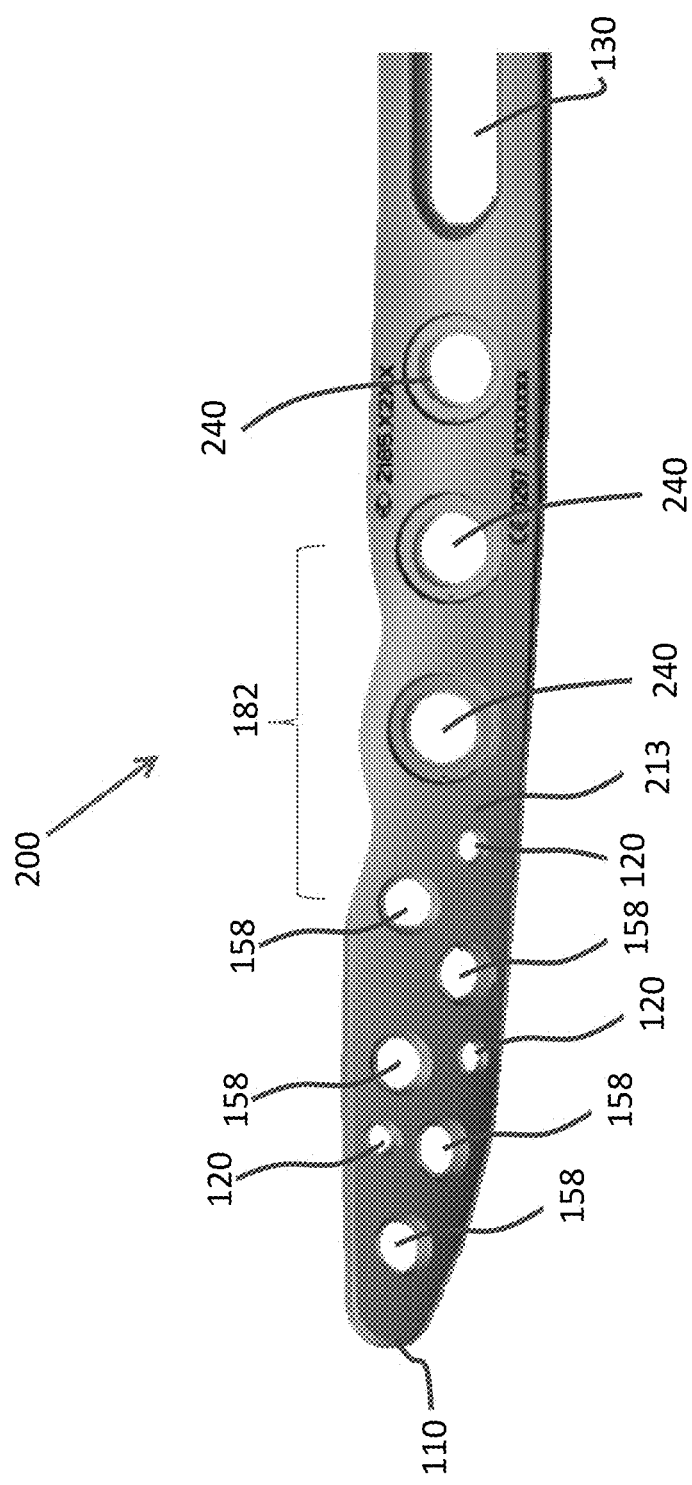
FIG. 6B is an alternative version of a posterolateral plate according to another embodiment.

FIG. 6B depicts an alternative version of posterolateral distal fibula plate 200. The plate 200 is substantially the same as that disclosed in FIG. 6A, with the addition of one or more scalloped edges 182. The scalloped edge or edges 182 may be positioned along the transition region 213 of the plate 200. The scalloped edge 182 may extend along one or both sides of the plate 200. As shown, the scalloped edge 182 may be positioned on a first side of the plate 200. The scalloped edge 182 may include a first recess or cutout positioned along the edge between the second and third syndesmotic holes 240 and a second recess or cutout positioned along the edge between the third syndesmotic hole 240 and the first locking hole 158. Because the posterolateral plate 200 is configured to sit on the posterior side of the fibula 50, syndesmotic screws 160, 170 (placed lateral to medial) or suture buttons 190 often cannot be placed through the plate 200. In some embodiments, these scallops 182 are configured to allow additional screws or suture buttons to be placed outside of the plate 200 and aids in these treatment options by not directly contacting the plate 200. In some embodiments, one or more fasteners (e.g., screws 160, 170) may be placed outside the plate 200, but in close proximity or in contact with the scalloped edge 182.

Figure 7:
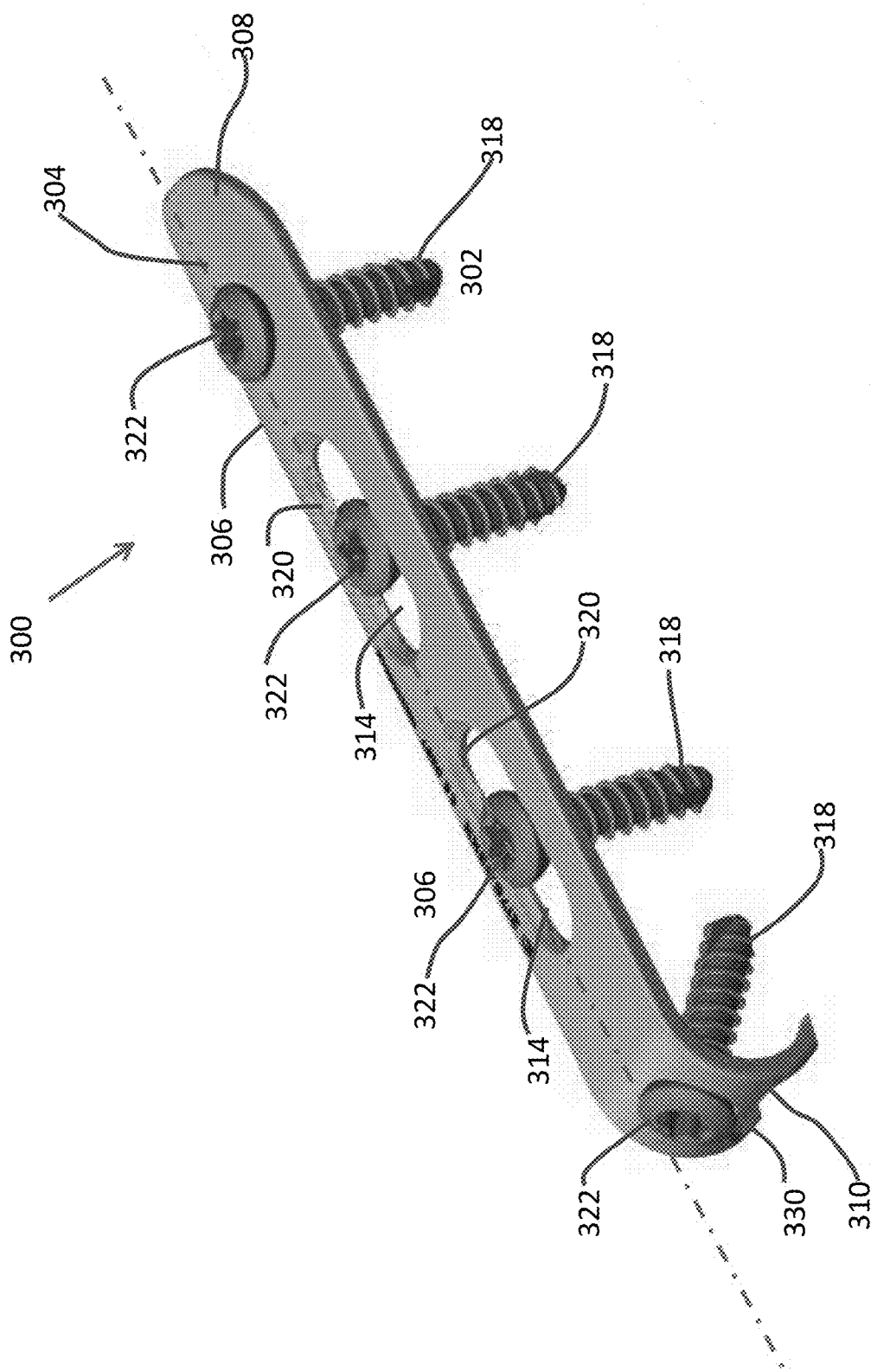
FIG. 7 is a perspective view of a hook plate according to a third exemplary embodiment.
Figure 8:
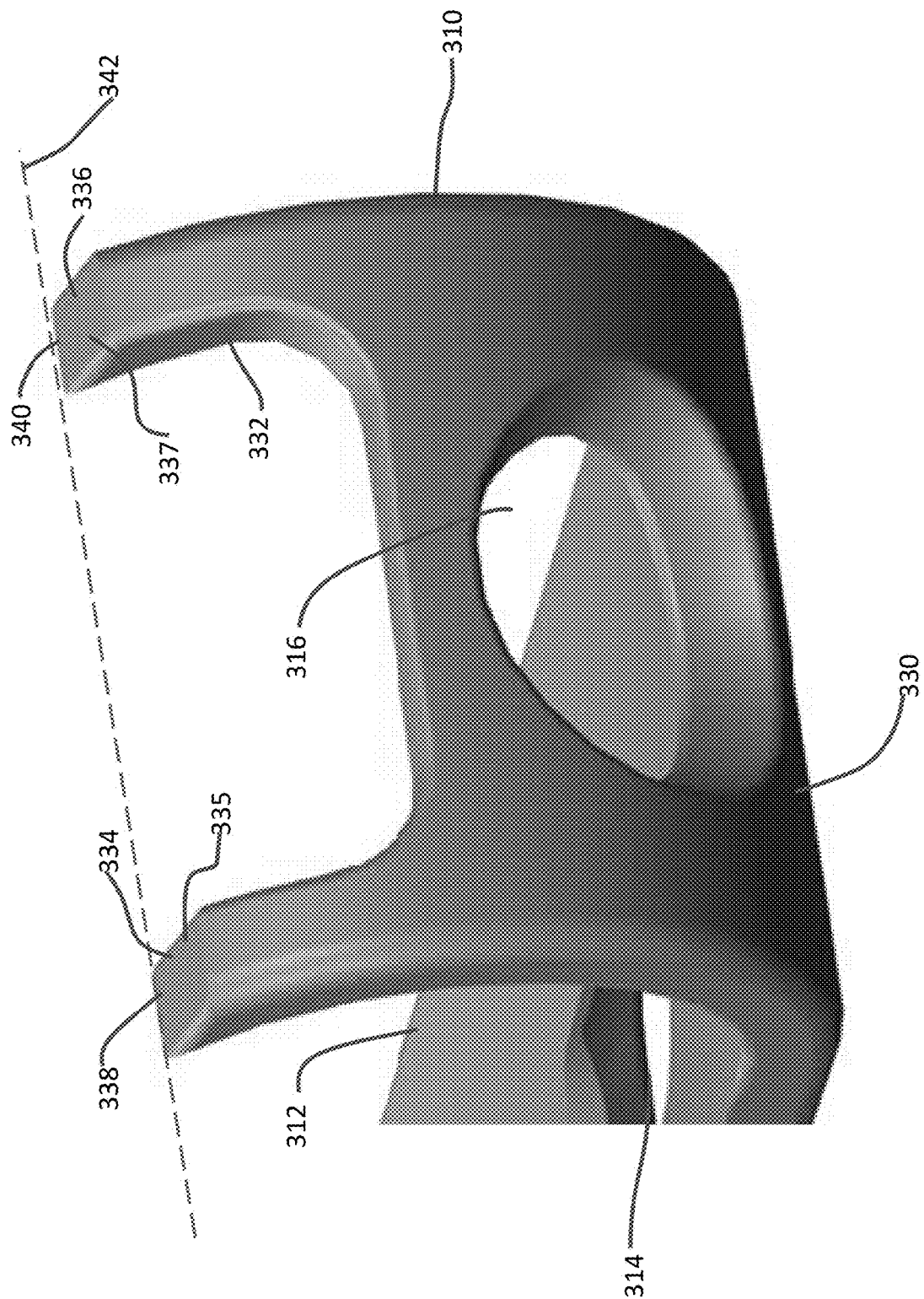
FIG. 8 is an enlarged perspective view of a distal end of the hook plate shown in FIG. 7.
Figure 9:
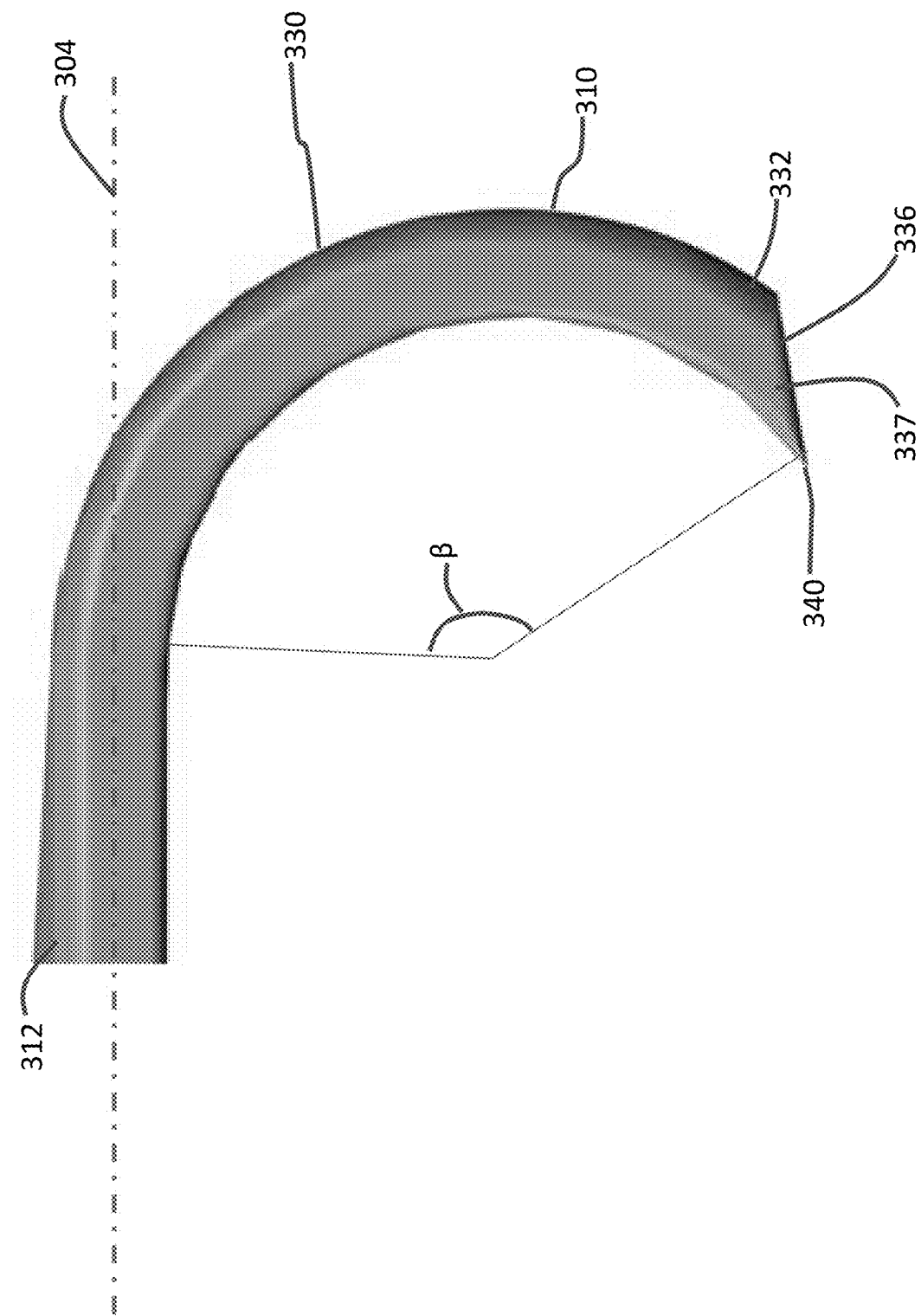
FIG. 9 is a side elevational view of the distal end of the hook plate shown in FIG. 8.

A third embodiment of a hook plate 300 ("plate 300") is shown in FIGS. 7-9. Plate 300 can be used for very distal fractures of the tibia or fibula, for example. Hook plate 300 has an elongate body 302 extending generally along a central longitudinal axis 304. Plate 300 has a generally planar top surface 306 extending between a proximal end 308 and a distal end 310. A body portion 312 extends between proximal end 308 and distal end 310. Plate 300 is symmetrical about a plane extending through central longitudinal axis 304 perpendicular to top surface 306.

In an exemplary embodiment, proximal end 308 includes a smooth, rounded face. The smooth, rounded face eliminates the potential for inadvertently engaging and ripping any adjoining tissue.

Body portion 312 is generally planar, with smooth, rounded surfaces, again to eliminate the potential for inadvertently engaging and ripping any adjoining tissue. Body portion 312 also includes a plurality of through-openings 314 formed therein. Through-openings 314 are elongate slots and allow for a range of securing member insertion locations. In an exemplary embodiment, two elongate through-openings 314 are provided, although those skilled in the art will recognize, depending on the length of plate 300 and through-openings 314, more or less than two through-openings 314 can be provided.

Through-openings 314 include generally smooth side walls to allow securing members 318 to be inserted at infinite locations along the length of each through-opening 314. A rib 320 may extend around the inner perimeter of through-opening 314 below top surface 306. In an exemplary embodiment, securing members 318 can be 3.5 mm or 4.0 mm non-locking screws and can provide up to 1 mm of compression or distraction. Securing members 318 engage rib 320 along an under surface of the head 322 of securing member 318 so that head 322 is largely, if not entirely, within through-opening 314 to minimize the amount of head 322 extending above top surface 306 of plate 300.

Through-openings 316 may be located at either end of plate 300. Through-openings 316 are shaft holes that can accept either one of locking and non-locking screws via the "stacked" design described above. A first through-opening 316 is located at proximal end 308 and a second through-opening 316 is located at distal end 310.

Referring to FIGS. 8 and 9, distal end 310 includes an arcuate surface 330 that extends away from the plane of body portion 312, and is used to capture the distal bone fragment of either the tibia or the fibula. Arcuate surface 330 extends in an arc having an angle β of between about 100 degrees and about 160 degrees, about 125 degrees and about 155 degrees, or about 135 degrees and about 150 degrees from body portion 312. At least one through-opening 316 extends through arcuate surface 330.

A most distal end 332 of arcuate surface 330 includes a hook assembly having two separate hooks 334, 336. Each hook 334, 336 includes a flat surface 335, 337, respectively and each flat surface 335, 337 includes a corresponding cutting edge 338, 340, respectively. Cutting edges 338, 340 extend along a single line 342 that is perpendicularly skew to longitudinal axis 304 and are used to engage and dig into bone material in the tibia or fibula.

With the exception of cutting edges 338, 340, all edges of arcuate surface 330 and hooks 334, 336 have smooth, rounded surfaces, again to eliminate the potential for inadvertently engaging and ripping any adjoining tissue.

Figure 10B:
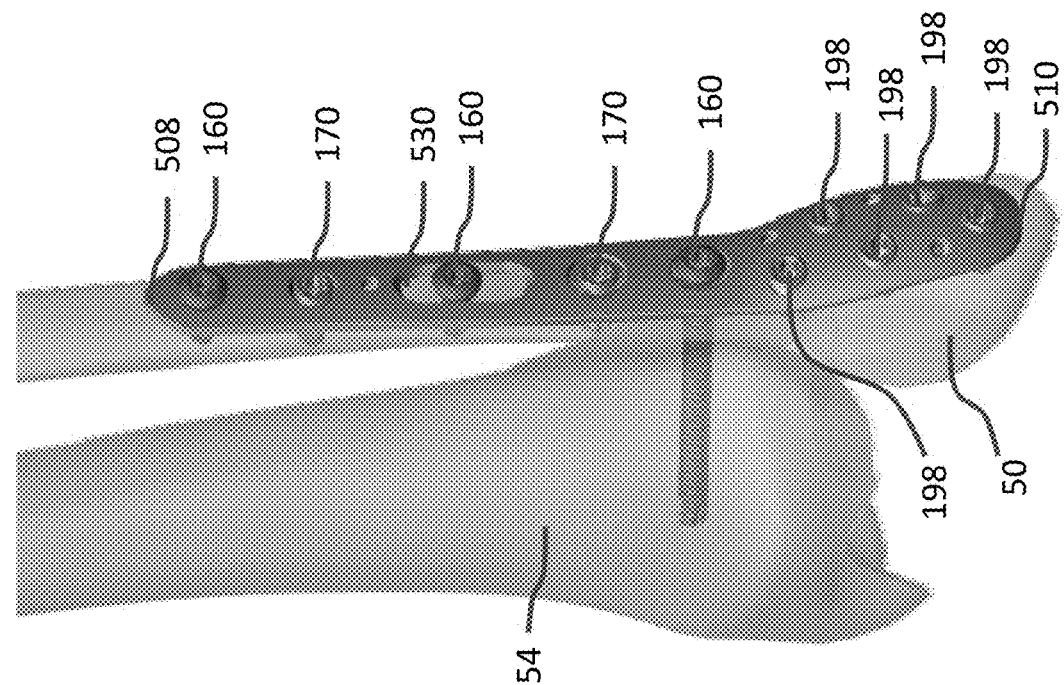
FIGS. 10A-10B depict a universal distal fibula plate according to yet another embodiment.
Figure 10A:
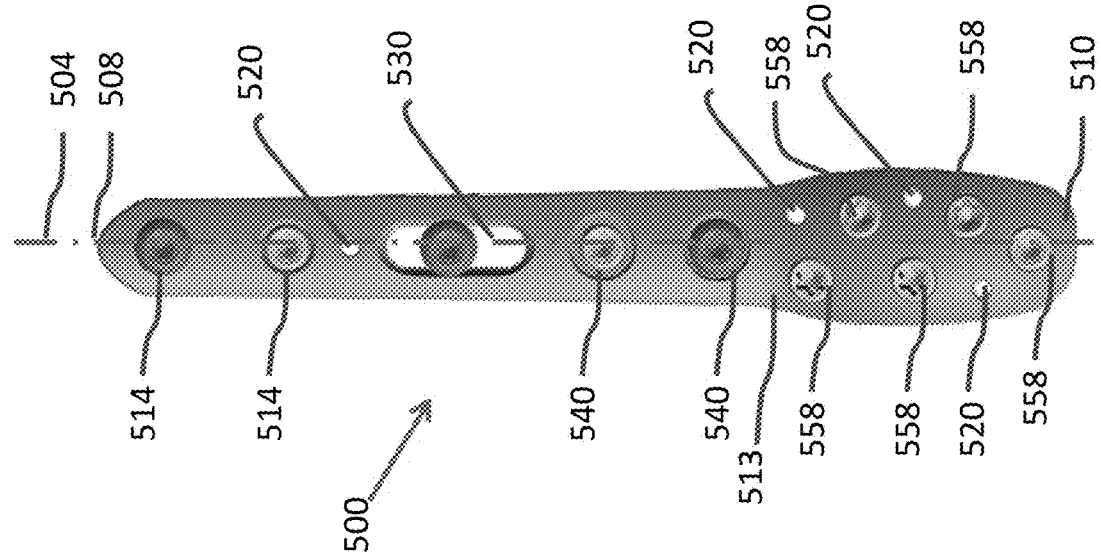

FIG. 10A depicts an embodiment of a universal distal fibula plate 500. In FIG. 10B, the universal distal fibula plate 500 is positioned against a distal portion of the fibula 50. This plate 500 is similar to the lateral distal fibula plate 100 described above. Plate 500 has an elongate body 502 extending generally along a central longitudinal axis 504. The plate 500 has a transition section 513 between proximal end 508 and distal end 510 where body 502 transitions from a generally planar portion proximate to proximal end 508 to an enlarged head portion proximate to distal end 510. The enlarged head portion may have a width greater than the width of the remainder of the plate 500. The enlarged distal head portion of the plate 500 may be bent or contoured to mimic the anatomy of the fibula 50 (e.g. the lateral malleolus of the fibula). In an exemplary embodiment, proximal end 508 and distal end 510 each includes smooth, rounded ends and edges. The plate 500 is generally symmetric about the longitudinal axis 504, such that plate 500 can accommodate left or right fibulas.

Similar to plate 100, plate 500 includes a plurality of different types of through-openings formed therein and extending therethrough. Through-openings 514, similar to through-openings 114 described herein, may feature a "stacked" design where the holes can accept both locking and non-locking fasteners 160, 170 or screws. In exemplary embodiments, the openings 114 are configured to accept fasteners including 3.5 mm or 4.0 mm screws, for example. Through-openings 514 may extend along longitudinal axis 504. Through-openings 520, similar to through-openings 120, may be sized and dimensioned to allow a K-wire to pass therethrough. Through-opening 530, similar to elongate slot 130, may extend along longitudinal axis 504, for example. Syndesmotic openings 540, similar to syndesmotic holes 140, are each configured to accept a suture button 190, a non-locking screw 160, or a locking screw 170. In particular, the syndesmotic holes 540 can accept 3.5 mm or 4.0 mm locking or non-locking screws. As best seen in FIG. 10B, at least one of the fasteners is positioned through the syndesmotic hole 540 has a length sufficient to engage the fibula 50 and the tibia 54. As shown, a non-locking fastener 160 connects the plate 500 to the fibula 50 and the tibia 54. In this embodiment, the other fasteners 160, 170 have a length sufficient to only engage the fibula 50.

Through-openings 558, similar to through holes 158, are provided in the enlarged distal head portion at the distal end 510 of plate 500. These holes 558 may be conically-threaded locking holes configured to receive locking fasteners 198. Holes 558 may be located along the width of plate 500 to provide a plurality of screw connections for a secure fixation to the fibula 50. One or more of the holes 558 may be replaced with a non-threaded hole 180 as described for the lateral distal fibula plate 100, which may be configured accept a non-locking fastener or screw 160 that can act as a suck-down screw. Plate 500 is universal and configured to secure the bone on left or right fibulas.

The bone plates 100, 200, 300, 500 described herein may be especially configured for treatment of an ankle fracture.

In particular, these plates 100, 200, 300, 500 may be especially suitable for treatment of the distal fibula including lateral distal fibula or the posterolateral distal fibula, and/or the distal tibia. These anatomic bone plates 100, 200, 300, 500 may facilitate improved treatment methods of ankle fractures and can provide a number of treatment options based on surgeon preference.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration. Thus, the features of one embodiment may be added or combined with the features of another embodiment.

What is claimed is:

1. A stabilization system comprising:
    a bone plate having an elongate body extending from a proximal end to a distal end along a longitudinal axis and having an enlarged head portion proximate the distal end, wherein the bone plate is symmetric about the longitudinal axis,
    wherein the bone plate comprises an elongated slot located along the longitudinal axis and having a length greater than its width,
    wherein the bone plate comprises a plurality of syndesmotic openings located along the longitudinal axis, wherein one of the syndesmotic openings is located adjacent to the elongated slot, the syndesmotic openings being sized and dimensioned to accept a suture button, a non-locking screw, or a locking screw,
    wherein each of the plurality of syndesmotic openings includes a first bore, a second bore disposed above the first bore and having a conical shape, and a third bore disposed above the second bore and having a bowl shaped inner surface,
    wherein the bone plate comprises a plurality of openings in the enlarged head portion, and
    wherein the first bore is threaded and the second and third bores are non-threaded,
    wherein the bowl shaped inner surface of the third bore includes a concavely curved sidewall and a flat annular surface extending laterally from the concavely curved sidewall to receive a lower surface of the suture button, wherein the flat annular surface laterally extends from a non-planar portion of the concavely curved sidewall, and wherein the conical shape of the second bore extends directly from the flat annular surface of the third bore to accommodate the non-locking screw.

2. The stabilization system according to claim 1, further comprising a first fastener configured to engage the elongated slot to secure the bone plate to the bone.

3. The stabilization system according to claim 2, further comprising a second fastener configured to engage one of the syndesmotic openings, wherein the second fastener is sized and dimensioned to engage the tibia and the fibula.

4. The stabilization system according to claim 1, wherein the plurality of openings in the enlarged head portion comprise conically-threaded locking holes.

5. The stabilization system according to claim 1, wherein one of the plurality of openings in the enlarged head portion is a non-threaded hole configured to receive a non-locking fastener in order to compress the bone plate to the bone.

6. The stabilization system according to claim 1, wherein an edge of the bone plate includes a scalloped section.

7. The stabilization system according to claim 6, wherein the plurality of syndesmotic openings includes a first syndesmotic opening, a second syndesmotic opening, and a third syndesmotic opening, wherein the plurality of openings in the enlarged head portion includes a first locking hole positioned proximate to the third syndesmotic opening, and wherein the scalloped section includes a first cutout positioned along the edge between the second and third syndesmotic holes and a second cutout positioned along the edge between the third syndesmotic hole and the first locking hole.

8. The stabilization system according to claim 1, wherein the enlarged head portion is contoured to mimic the anatomy of the lateral malleolus of the fibula.

9. The stabilization system according to claim 1, wherein the bone plate is configured to contact the distal fibula.

10. The stabilization system according to claim 1, wherein the bone plate can accommodate left or right fibulas.

11. A stabilization system comprising:
    a bone plate having an elongate body extending from a proximal end to a distal end along a longitudinal axis and having an enlarged head portion proximate the distal end, wherein the bone plate is symmetric about the longitudinal axis,
    wherein the bone plate comprises first and second stacked openings located along the longitudinal axis and positioned proximate to the proximal end of the bone plate, the first and second stacked openings configured to accept either locking or non-locking fasteners,
    wherein the bone plate comprises an elongated slot located along the longitudinal axis having a length greater than its width, wherein the elongated slot is located adjacent to the second stacked opening,
    wherein the bone plate comprises a plurality of syndesmotic openings located along the longitudinal axis, wherein one of the syndesmotic openings is located adjacent to the elongated slot, the syndesmotic openings being sized and dimensioned to accept a suture button, a non-locking screw, or a locking screw,
    wherein each of the plurality of syndesmotic openings includes a first bore, a second bore disposed above the first bore and having a conical shape, and a third bore disposed above the second bore and having a bowl shaped inner surface, and
    wherein the bone plate comprises a plurality of openings in the enlarged head portion, and
    wherein the first bore is threaded and the second and third bores are non-threaded,
    wherein the bowl shaped inner surface of the third bore includes a concavely curved sidewall and a flat annular surface extending laterally from the concavely curved sidewall to receive a lower surface of the suture button, wherein the flat annular surface laterally extends from a non-planar portion of the concavely curved sidewall, and wherein the conical shape of the second bore extends directly from the flat annular surface of the third bore to accommodate the non-locking screw.

12. The stabilization system according to claim 11, further comprising a first fastener configured to engage the elongated slot to secure the bone plate to the bone.

13. The stabilization system according to claim 12, further comprising a second fastener configured to engage one of the syndesmotic openings, wherein the second fastener is sized and dimensioned to engage the tibia and the fibula.

14. The stabilization system according to claim 11, wherein the plurality of openings in the enlarged head portion comprise conically-threaded locking holes.

15. The stabilization system according to claim 11, wherein one of the plurality of openings in the enlarged head portion is a non-threaded hole configured to receive a non-locking fastener in order to compress the bone plate to the bone.

16. The stabilization system according to claim 11, wherein an edge of the bone plate includes a scalloped section.

17. The stabilization system according to claim 16, wherein the plurality of syndesmotic openings includes a first syndesmotic opening, a second syndesmotic opening, and a third syndesmotic opening, wherein the plurality of openings in the enlarged head portion includes a first locking hole positioned proximate to the third syndesmotic opening, and wherein the scalloped section includes a first cutout positioned along the edge between the second and third syndesmotic holes and a second cutout positioned along the edge between the third syndesmotic hole and the first locking hole.

18. The stabilization system according to claim 11, wherein the enlarged head portion is contoured to mimic the anatomy of the lateral malleolus of the fibula.

19. The stabilization system according to claim 11, wherein the bone plate is configured to contact the distal fibula.

20. The stabilization system according to claim 11, wherein the bone plate can accommodate left or right fibulas.

* * * * *